(12) United States Patent  (10) Patent No.: US 8,267,915 B2
Daly et al.  (45) Date of Patent: Sep. 18, 2012

(54) DUAL WELL PORT DEVICE

(75) Inventors: Katie Daly, Revere, MA (US); Kristian DiMatteo, Waltham, MA (US); Eric Houde, Glens Falls, NY (US)

(73) Assignee: Navilyst Medical, Inc., Marlborough, MA (US)

( * ) Notice: Subject to any disclaimer, the term of this patent is extended or adjusted under 35 U.S.C. 154(b) by 1390 days.

(21) Appl. No.: 10/768,479

(22) Filed: Jan. 29, 2004

(65) Prior Publication Data
US 2005/0171502 A1   Aug. 4, 2005

(51) Int. Cl.
*A61M 31/00* (2006.01)
*A61M 37/00* (2006.01)
*A61K 9/22* (2006.01)

(52) U.S. Cl. ............... 604/502; 604/500; 604/288.01; 604/891.1; 604/288.04; 604/93.01

(58) Field of Classification Search ............ 604/288.02, 604/288.03, 288.04, 93.01, 891.1, 500, 502, 604/288.01
See application file for complete search history.

(56) References Cited

U.S. PATENT DOCUMENTS

| | | | |
|---|---|---|---|
| 3,159,175 A | 12/1964 | Macmillan | |
| 3,477,438 A | 11/1969 | Allen et al. | |
| 3,541,438 A | 5/1970 | Nelsen et al. | |
| 3,525,357 A | 8/1970 | Koreski | |
| 3,669,323 A * | 6/1972 | Harker et al. ............... | 222/490 |
| 3,674,183 A | 7/1972 | Venable et al. | |
| 3,811,466 A | 5/1974 | Ohringer | |
| 3,955,594 A | 5/1976 | Snow | |
| 4,143,853 A | 3/1979 | Abramson | |
| 4,447,237 A | 5/1984 | Frisch et al. | |
| 4,610,665 A | 9/1986 | Matsumoto et al. | |
| 4,692,146 A * | 9/1987 | Hilger ...................... | 604/288.01 |
| 5,009,391 A | 4/1991 | Steigerwald | |
| 5,084,015 A * | 1/1992 | Moriuchi ................. | 604/288.02 |
| 5,167,638 A | 12/1992 | Felix et al. | |
| 5,205,834 A | 4/1993 | Moorehead et al. | |
| 5,249,598 A | 10/1993 | Schmidt | |

(Continued)

FOREIGN PATENT DOCUMENTS
EP   0128525   12/1984
(Continued)

OTHER PUBLICATIONS msn Encarta Dictionary definition of "base".*

(Continued)

*Primary Examiner* — Kevin C Sirmons
*Assistant Examiner* — Bradley Thomas, Jr.
(74) *Attorney, Agent, or Firm* — Bingham McCutchen LLP

(57) ABSTRACT

A port for implantation within a body, comprises a housing having proximal and distal surfaces and a side surface wherein, the proximal surface faces outward toward the skin, the distal surface faces inward away from the skin and the side surface extends between the proximal and distal surfaces. A first well formed within the housing includes a first opening in the proximal surface and a second well formed in the housing adjacent to the first well has a second opening formed in the proximal surface. First and second outlet openings formed on the side surface of the port are in fluid communication with the first and second wells, respectively, and are separated from one another by a distance substantially equal to a distance separating lumens of a dual lumen catheter to which the port is to be connected.

8 Claims, 4 Drawing Sheets

U.S. PATENT DOCUMENTS

| | | |
|---|---|---|
| 5,396,925 A | 3/1995 | Poli et al. |
| 5,453,097 A | 9/1995 | Paradis |
| 5,707,357 A | 1/1998 | Mikhail et al. |
| 5,755,780 A * | 5/1998 | Finch et al. ............... 623/1.24 |
| 5,944,698 A | 8/1999 | Fischer et al. |
| 6,056,717 A | 5/2000 | Finch et al. |
| 6,152,909 A | 11/2000 | Bagaoisan et al. |
| 6,210,366 B1 | 4/2001 | Sanfilippo |
| 6,306,124 B1 | 10/2001 | Jones et al. |
| 121,530 A1 | 9/2002 | Socier |
| 6,610,031 B1 | 8/2003 | Chin |
| 6,726,063 B2 | 4/2004 | Stull et al. |
| 2002/0121530 A1 | 9/2002 | Socier |
| 2004/0186444 A1 | 9/2004 | Daly et al. |
| 2005/0010176 A1 | 1/2005 | Dikerman et al. |
| 2005/0027261 A1 | 2/2005 | Weaver et al. |

FOREIGN PATENT DOCUMENTS

| | | |
|---|---|---|
| EP | 0 366 814 | 5/1990 |
| EP | 0474069 | 3/1992 |
| FR | 2 508 008 | 12/1982 |
| FR | 2508008 | 12/1982 |
| GB | 2 102 398 | 2/1983 |
| WO | 95/16480 | 6/1995 |
| WO | 99/42166 | 8/1999 |
| WO | 00/44419 | 8/2000 |
| WO | 03/084832 | 10/2003 |
| WO | 2005/023355 | 3/2005 |

OTHER PUBLICATIONS

Encarta: definition of "base": http://encarta.msn.com/dictionary_1861589078/base.html.*

* cited by examiner

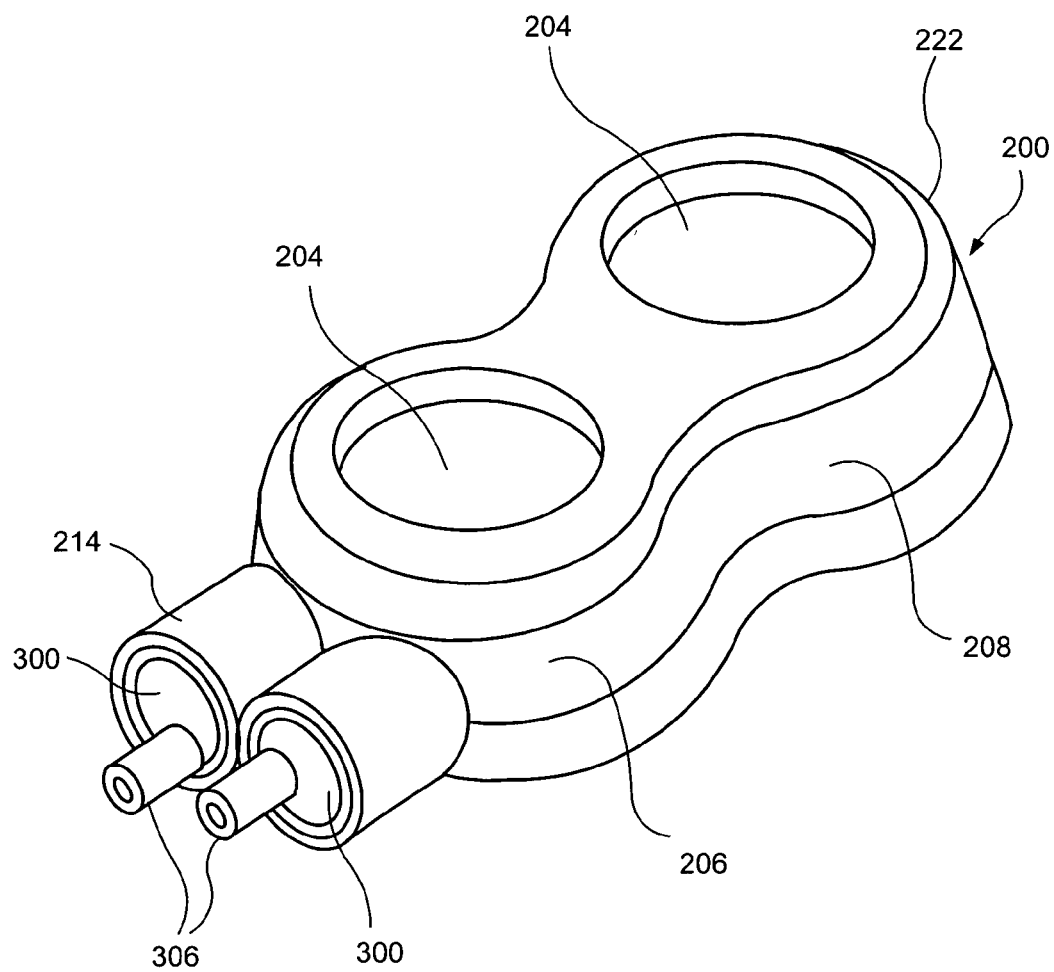
F I G. 6

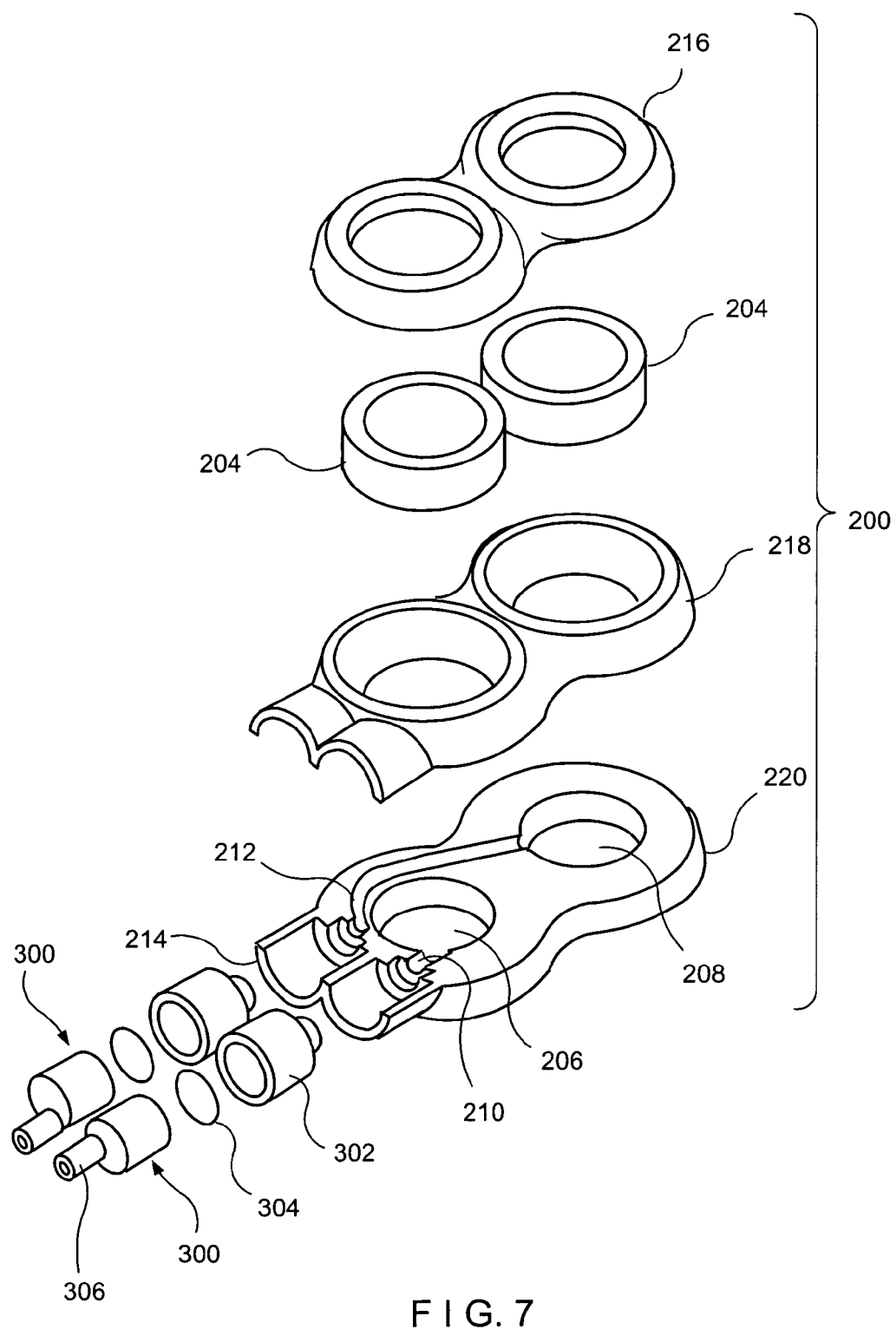
F I G. 7

DUAL WELL PORT DEVICE

The present application incorporates by reference the entire disclosure of (1) U.S. patent application Ser. No. 10/768,571 entitled "Pressure Activated Safety Valve With Anti-Adherent Coating" filed on Jan. 29, 2004 naming Karla Weaver and Paul DiCarlo as inventors; (2) U.S. patent application Ser. No. 10/768,571 entitled "Pressure Activated Safety Valve With Anti-Adherent Coating" filed on Jan. 29, 2004 naming Karla Weaver and Paul DiCarlo as inventors; (3) U.S. patent application Ser. No. 10/768,629 entitled "Stacked Membrane For Pressure Actuated Valve" filed on Jan. 29, 2004 naming Karla Weaver and Paul DiCarlo as inventors; and (4) U.S. patent application Ser. No. 10/768,855 entitled "Pressure Actuated Safety Valve With Spiral Flow Membrane" filed on Jan. 29, 2004 naming Karla Weaver and Paul DiCarlo as inventors.

BACKGROUND OF THE INVENTION

Many medical procedures require repeated and prolonged access to a patient's vascular system. For example, chemotherapy, paraternal nutrition antibiotic regimens, blood withdrawals and other similar treatments require such repeated access to the patient's vascular system. It is impractical and dangerous to insert and remove the catheter for each session. Thus, the needle and catheter are generally implanted semi-permanently with a distal portion of the assembly remaining within the patient in contact with the vascular system while a proximal portion of the catheter remains external to the patient's body. Alternatively, the proximal portion may be implanted subcutaneously with a port formed therein for access via, for example, a syringe. In many cases, such a port will be implanted subcutaneously in the patient's arm or chest, to keep it protected while affording easy access, and consists of a housing with one or more wells to receive the therapeutic agents.

It is often necessary to infuse into the patient therapeutic agents that are not compatible with each other. For example, certain chemotherapy agents are incompatible with one another and, therefore, require special handling during therapeutic sessions. In some cases, the therapeutic agents are fluids that cannot be mixed together outside of the body, but which will preferably be infused together or within a certain period of time. Some of these fluids cannot be infused through the same lumen because they may coagulate or form a precipitate that clogs the port or catheter lumen. In other instances, the fluids may be incompatible for other reasons, and are therefore kept separate until they reach the patient's blood stream. This has conventionally been achieved by employing, for example, a separate catheter for each of the agents with distal ends of the catheters opening to the bloodstream in proximity to one another. Alternatively, a dual lumen catheter may be used, with each lumen containing a different one of the agents.

Providing two unmixable therapeutic fluids to a dual lumen catheter or to two separate catheters near each other presents challenges, since a conventional port cannot be used to inject both fluids. Ports are generally not implanted near one another because of the surgery required to insert each port in place, and the additional complications that may arise as a result of the port residing in an area. A dual well port device may be used, with two ports formed within a single housing, each port being connectable to a different catheter or to a different lumen of a dual lumen catheter. However, conventional dual well port devices are larger than single port devices, and may be difficult to place in the patient's body. In addition, an adapter is often required to connect a dual lumen catheter to conventional dual well port devices, because the distance between the outlets of the dual well port device is greater than the separation between the two lumens of the catheter.

SUMMARY OF THE INVENTION

In one aspect, the present invention is directed to a port for implantation within a body, comprising a housing having a proximal surface, a distal surface and a side surface wherein, when the port is implanted within a body in a desired orientation, the proximal surface faces outward toward the skin, the distal surface faces inward away from the skin and the side surface extends between the proximal and distal surfaces and first and second wells formed within the housing, and including, respectively, first and second openings in the proximal surface in combination with first and second outlet openings formed on the side surface separated from one another by a distance substantially equal to a distance separating lumens of a dual lumen catheter to which the port is to be connected, wherein the first outlet opening is in fluid communication with the first well and the second outlet opening is in fluid communication with the second well.

The present invention is also directed to a method of infusing fluids to a patient, comprising the steps of attaching a dual lumen catheter to a blood vessel of the patient and implanting subcutaneously a port including first and second openings separated by a distance substantially equal to a distance between the dual lumens of the catheter, wherein the first opening is in fluid communication with a first well of the port and the second opening is in fluid communication with a second well of the port in combination with the steps of connecting the dual lumen catheter to first and second openings of the port and providing first and second fluids to the first and second wells, respectively.

BRIEF DESCRIPTION OF THE DRAWINGS

FIG. 6 is a perspective view of a fourth embodiment of the dual body port according to the present invention; and FIG. 7 is an exploded view of the dual body port of FIG. 6.

DETAILED DESCRIPTION

Figure 1:
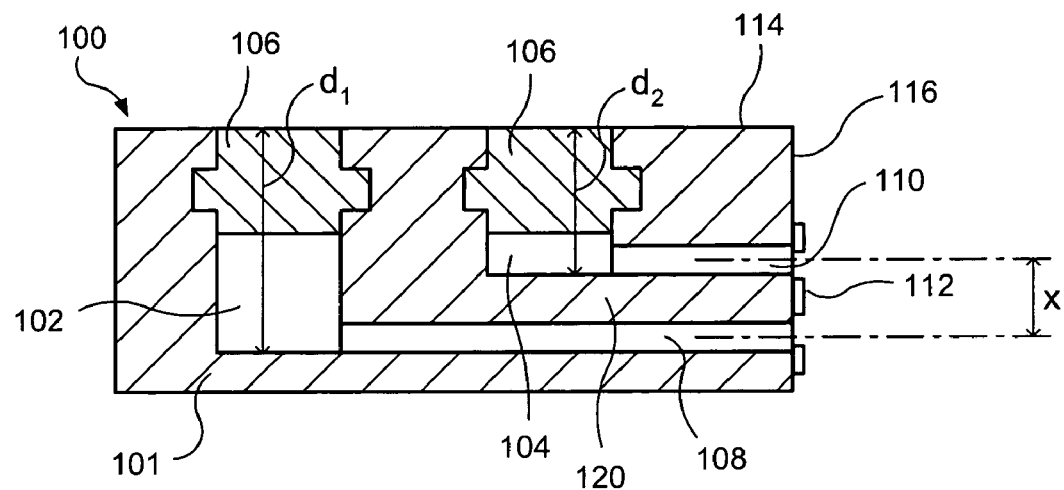
FIG. 1 is across sectional side view showing a dual body port according to an embodiment of the invention.

The present invention may be further understood with reference to the following description and the appended drawings, wherein like elements are referred to with the same reference numerals. The present invention is related to medical devices that are used to access the vascular system of a patient. In particular, the present invention relates to access ports used to inject therapeutic agents into the patient vasculature.

Semi-permanently placed ports may be useful for a variety of medical procedures which require repeated access to a patient's vascular system. For example, chemotherapy infusions may be repeated several times a week for extended periods of time. For safety reasons, as well as to improve the comfort of the patient, injections of these therapeutic agents may be better carried out with an implantable, semi-permanent vascular access port. There are many conditions that require chronic venous supply of therapeutic agents, nutrients, antibiotics, blood products or other fluids to the patient or withdrawing blood from the patient that may benefit from implantable access ports, to avoid repeated insertion of a needle into the patient's blood vessels. Thus, those skilled in the art will understand that the invention may be used in conjunction with any of a wide variety of procedures which require long term implantation of ports within the body. The port is a device placed subcutaneously in the patient (e.g., the arm or chest) to selectively provide access to the vascular system. The port may include a self sealing surface that can be pierced through the skin, for example by a needle, to inject the therapeutic agents into the vascular system.

Implantable catheters are typically inserted under the patient's skin, and have a distal end which includes a needle used to enter a blood vessel. The devices also have a proximal end extending outside the body for connection with an outside line. These semi-permanent catheters may be sutured to the patient's skin to maintain them in place while the patient goes about his or her normal occupations.

In many therapeutic regimes it becomes necessary to infuse fluids that react negatively if they are mixed together outside of the patient's bloodstream, but that are injected together to mix in the bloodstream. These fluids may be chemotherapy agents that develop excessive toxicity or lose their potency if they are mixed prior to reaching the patient's blood. Some antibiotics may also have to be injected separately from, but at the same time as, other fluids. Dual well port devices are currently used to infuse these unmixable fluids, so that each of the fluids is injected into one of the device's wells, without contacting the other fluid prior to entering the blood stream. Such a dual lumen catheter or, alternatively, a pair of separate single lumen catheters, may be connected to the ports to carry the fluids to the patient's blood vessel. The wells of these dual port devices are separated and the channels leading from the wells to the catheter(s) are also separate to prevent mixing of the fluids before they exit the distal end of the catheter(s). Due to size constraints, the wells of the port are often too far apart to allow direct connection to a dual lumen catheter. Therefore, adapters and connectors may be necessary to couple the dual well port to a catheter or catheters, increasing the size and complexity of the devices being implanted.

According to exemplary embodiments of the present invention, a dual well port device is provided which does not necessitate the use of adapters or connectors, and which can be coupled directly to a dual lumen catheter. The dual well port according to the present invention includes a dual outlet at which two channels extending from the dual wells converge to permit a fluid connection with the dual lumen catheter. The channels are disposed a small distance apart (i.e., a distance comparable to the distance between lumens of a dual lumen catheter). Accordingly, the catheter may be connected directly to the outlet of the dual well port, without additional components being necessary. The ability to connect the port directly to a dual lumen catheter simplifies the surgical procedure necessary to implant the device, and reduces the size and number of the elements that have to be implanted.

Figure 2:
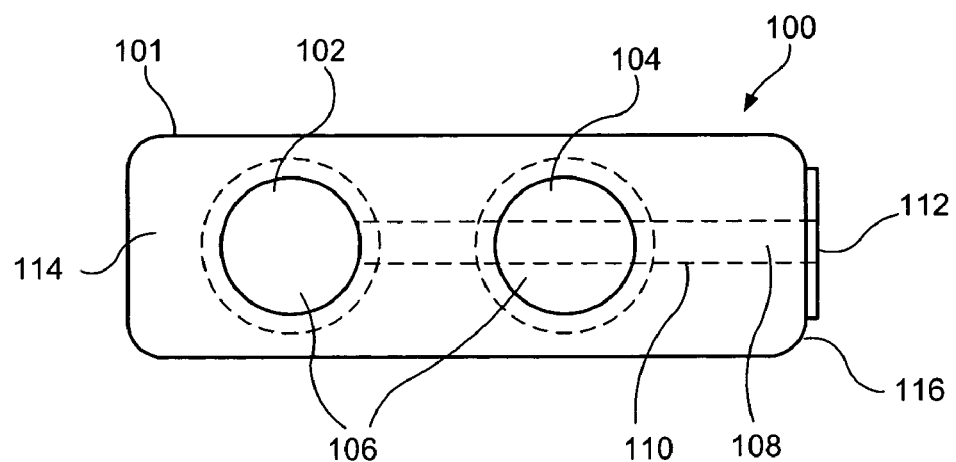
FIG. 2 is a top plan view of the dual body port shown in FIG. 1.

FIGS. 1 and 2 show an exemplary embodiment of a dual well port 100 according to the present invention. The port 100 comprises a housing 101 in which two wells 102 and 104 are formed. Two unmixable therapeutic agents to be administered to the patient may be inserted via, for example, a syringe or other injection means, to the wells 102 and 104 so that they remain separated until they reach the patient's blood stream. The wells 102, 104 each open through a top surface 114 of the port 100, and extend a selected depth into the port 100. Those skilled in the art will understand that the term "top" surface as used herein does not refer to an orientation with respect to the vertical, but rather refers to a surface which, when the device is implanted in a desired configuration, will face the surface of the skin. That is, the "top" surface 114 will lie just underneath and substantially parallel to the skin so that the openings formed therein are accessible from outside the skin. Septums 106 are used to allow access to the ports and may also serve as a barrier between the interior well of the port and the surrounding tissue. This prevents, for example, chemotherapy or other harmful drugs from contacting the tissue in quantities that may prove damaging. Each septum 106 may, for example, be formed of silicone or any other suitable polymeric element that can be repeatedly pierced with a needle, and which re-seals itself after the needle has been removed. The life span of such septums 106 typically is on the order of thousands of punctures, before they can no longer reliably re-seal themselves. Those skilled in the art will understand that this life span may vary based on a number of factors including, for example, a gage of needle which is used to puncture the septum 106.

The wells 102 and 104 extend, respectively, to channels 108 and 110 which lead to an exit portion of the port 100 which may be formed, for example, as a dual outlet 112. Each of the channels 108, 110 is in fluid connection with a corresponding one of the wells 102, 104, and is separate the other of the wells 102, 104 and the other of the channels 108, 110. As shown more clearly in FIG. 2, the channels 108, 110 are disposed within the housing 101 to minimize a distance between the centers of the channels. In the example shown, the channels 108, 110 extend substantially parallel to one another and to the top surface 114 in different planes. Specifically, the channel 108 lies at a greater depth from the top surface 114 than does the channel 110. For efficient draining of fluids from the wells 102, 104, each of the channels 108, 110, is connected to the bottom surface of the respective well 102, 104. Accordingly, a depth d1 of the well 102 is greater than a depth d2 of the well 104, as measured from the top surface 114.

This configuration of the wells 102, 104 and the channels 108, 110 shown in FIGS. 1 and 2 provides a compact and easily manufactured dual well port 100. In conventional designs, wells are formed at substantially similar depths, so that channels extending from the center of the wells have must either be separated at least by the sum of the radii of the wells, or must follow a complex path to reach outlets adjacent to one another. In the exemplary embodiment, the channels 108, 110 may be substantially straight passages with no curves, which are relatively easy to manufacture. The distance X between the channels 108 and 110 may be selected as small as necessary, limited only by the structural properties of the material forming a partition 120 between the channels 108, 110. For example, the distance X between the centers of the channels 108 and 110 may be selected to match a distance between lumens of a dual lumen catheter which is to be connected thereto. This catheter may then be connected directly to the channels 108, 110. Those skilled in the art will understand that the distance X may vary over the lengths of the channels 108, 110 but that this distance may preferably be substantially equal to a spacing between the lumens of the double lumen catheter to which the port 100 is to be coupled at the outlet 112.

Figure 3:
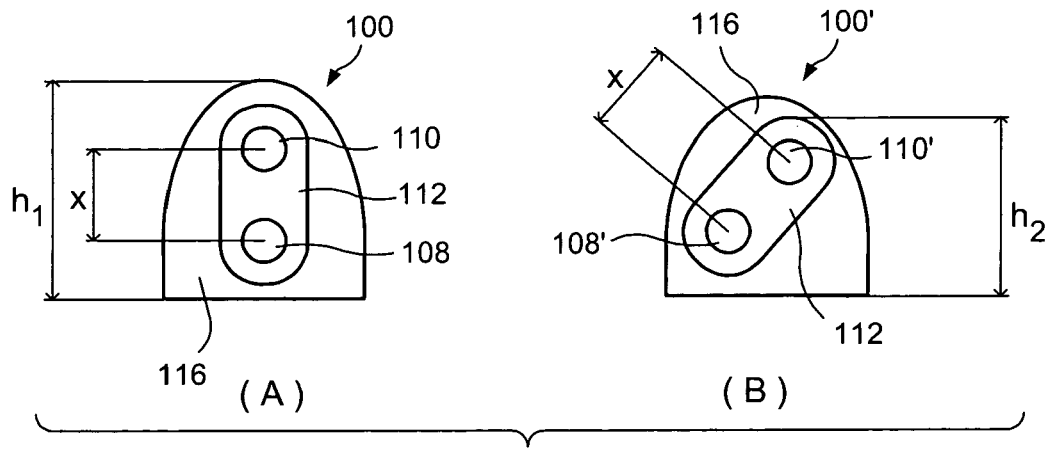
FIG. 3A is a front view showing a first embodiment of an outlet for the dual body port of FIG. 1.
FIG. 3B is a front view showing a second embodiment of an outlet for the dual body port of FIG. 1.

FIGS. 3A and 3B show first and second embodiments of a face 116 of the device on the dual outlet 112 is formed. The embodiment shown in FIG. 3A corresponds to the port 100 shown in FIGS. 1 and 2, where the channels 108, 110 are disposed vertically one directly above the other. In some applications, it may be desirable to further reduce a thickness of the device. Accordingly as shown in FIG. 3B, the channels 108, 110 may be offset from one another laterally and/or vertically with respect to the surface 116 to give the port 100' a more slender profile. Once again, those skilled in the art will understand that the term vertical refers to a direction along the device which, when the device is implanted, will be substantially perpendicular to a portion of skin against which the surface 114 is to rest and laterally describes a distance along the device in a direction substantially parallel to the portion of skin against which the surface 114 is to rest. For example, the channels 108' and 110' of the port 110 of FIG. 3B may extend from opposite edges of their respective wells rather than from centers thereof as shown in FIG. 2. The distance X between the centers of channels 108', 110' is the same as that between channels 108, 110, but the additional depth of one well with respect to the other well may be reduced to less than X. Offsetting the centers of channels 108', 110' thus reduces an overall height h2 of port 100' relative to the height h1 of port 100.

Figure 4:
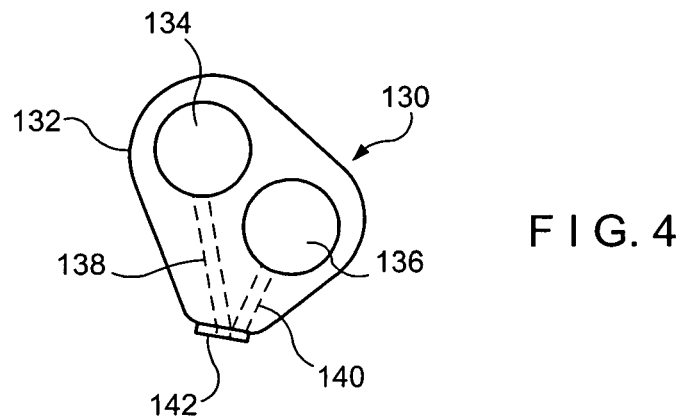
FIG. 4 is a top plan view of a second embodiment of the dual body port according to the present invention.
Figure 5:
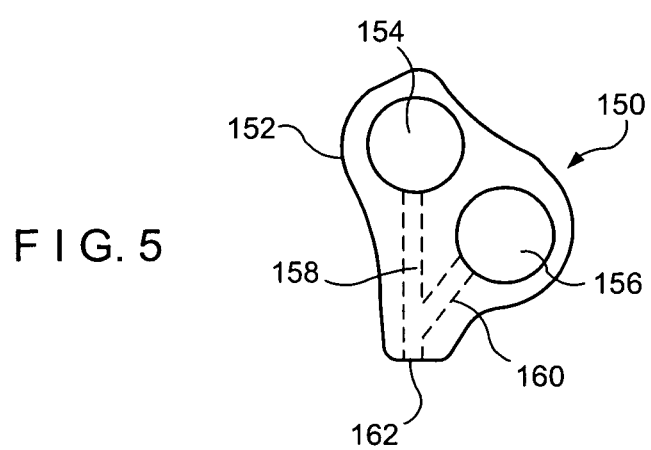
FIG. 5 is a top plan view of a third embodiment of the dual body port according to the present invention.

For certain applications, it may be necessary to provide wells of a dual well port device that are laid out in a particular orientation with respect to an outlet, and thus with respect to a catheter coupled to the port and leading to a blood vessel. In that case, the dual outlet of the port is constructed so that the desired orientation is obtained when the device is implanted with the septums 106 facing in a desired outward direction (e.g., toward and outer surface of the skin). FIGS. 4 and 5 depict exemplary embodiments of the dual well port according to the invention, showing a desired orientation of the outlets and the wells with respect to one anther. For example, FIG. 4 shows a port 130 having wells 134, 136 disposed adjacent to one another in substantially the same plane with channels 138 and 140 extending toward an outlet 142 diagonally with respect to one another. The openings of the channels 138 and 140 at the outlet 142 are arranged adjacent to one another in a plane which, when the device is implanted beneath the skin in a desired orientation, will be substantially parallel to an outer surface of the skin so that a dual lumen catheter attached thereto, will show a minimum profile as it passes from the port 130 to the blood vessel. Of course, those skilled in the art will understand that the orientation of the channels 138, 140 at the outlet 142 may be set to any desired configuration with respect to a plane of the skin (e.g., substantially perpendicular to the plane of the skin or at any angle with respect to the plane of the skin) to accommodate any desired orientation of a dual lumen catheter coupled thereto.

FIG. 5 shows another embodiment of a dual lumen port according to the present invention with a specified orientation of the outlet and wells with respect to one another. In this case, channels 158, 160 extend respectively from wells 154, 156 in a plane which, when the device is implanted beneath the skin in a desired orientation, is substantially perpendicular to a plane of the skin. The channels 158, 160 extend to openings at an outlet 162 for coupling to a dual lumen catheter. In this embodiment, the channels 158,160 lie at different depths within the housing 152 with respect to a plane in which outer surfaces of the septums lie, so that they extend one above the other at least near the outlet 162. It will be apparent to those skilled in the art that different layouts of the wells and channels may be constructed, depending on the requirements of individual situations. Accordingly, different combinations of well orientations and channel outlet orientations may be achieved, to obtain a shape of the dual well port that is appropriate to the specified medical procedure. For certain applications, the outlet may combine the openings of the two channels, so that the fluids separately injected into the wells can be mixed in the channels prior to exiting the dual well port.

For certain specialized applications, the height of the dual well port is reduced to a minimum value. FIG. 6 shows an exemplary embodiment according to the present invention of a port 200 having a reduced thickness. In this example, the dual well port 200 comprises two wells 206, 208, each sealed by a septum 204. The port 200 achieves a thin profile by slightly widening its footprint. As shown more clearly in FIG. 7, channels 210 and 212 connect wells 206 and 208, respectively, to the outlet 214. In the exemplary embodiment, the channel 210 is substantially straight, and extends a short distance from one edge of the well 206 to the outlet 214. In contrast, the channel 212 is longer, and curves around the outer perimeter of the well 206 to fluidly connect the well 208 to the outlet 214. In this configuration, the channels 210, 212 do not overlie one another, but instead are formed in substantially the same plane. The bottom surfaces of the wells 206, 208 also are in substantially the same plane, generally corresponding to the plane in which the channels lie.

As shown in FIG. 7, the exemplary dual well port according to the invention may be manufactured from several separate pieces which may be combined in a final assembly step. For example, the housing 222 of the port 200 may be formed by three separate parts joined together. Upper housing 216, center housing 218 and lower housing 220 may be formed separately, and may be joined together using methods known in the art. For example, gaskets or welds may be employed to connect the housing components 216, 218, 220 to form a leak-proof housing 222. The components of the dual well port 200 may be formed by molding, machining or any other conventional method suitable for the materials used and the geometry of the wells and channels. In one exemplary embodiment, the port 200 may be formed of a plastic or polymeric material, however metals (such as titanium) and other bio-compatible materials may be used as well.

A flow control valve or valves may also be provided either as part of the dual well port according to the invention, or as an add-on element that may be fitted thereto. For example, as shown in FIGS. 6 and 7, a pressure actuated valve 300 may be fitted into the outlet 214 for each of the openings of the channels 210, 212. Inside a housing 302 thereof, the pressure actuated valve 300 may include a flow control membrane 304, designed to allow fluid to flow therethrough when a flow pressure reaches a selected threshold value and the prevent flow when the fluid pressure is less than the threshold value. The flow control membrane 304 may be designed to make the pASV a three-way valve meaning that the valve permits infusion (i.e., flow into the patient), aspiration (i.e., flow out of the patient) or remains closed to permit no flow. The pressure actuated valve 300 may also include a nozzle portion 306 that is shaped to fluidly connect with an attachment portion of a dual lumen catheter. (Not shown in the drawing). As will be apparent to those skilled in the art, various conventional methods of attaching valve 300 to outlet 214 may be used, without departing from the scope of the invention. It will also be apparent that elements such as valve 300 described with reference to the embodiment of FIGS. 7, 8 may also be utilized in other embodiments according to the invention. Those of skill in the art will understand that there may be various types of flow control valves that can be attached to the dual well port.

The present invention has been described with reference to specific embodiments, and more specifically to a two well port for use with a central catheter. However, other embodiments may be devised that are applicable to other medical devices, without departing from the scope of the invention. Accordingly, various modifications and changes may be made to the embodiments, without departing from the broadest spirit and scope of the present invention as set forth in the claims that follow. The specification and drawings are accordingly to be regarded in an illustrative rather than restrictive sense.

What is claimed is:

1. A method of infusing fluids to a patient, comprising:
   attaching a dual lumen catheter to a blood vessel of the patient;
   implanting a port subcutaneously, the port including a proximal surface and first and second outlet openings separated by a distance substantially equal to a distance between the dual lumens of the catheter, wherein the first outlet opening is in fluid communication with a first base of a first well of the port at a first depth from the proximal surface and the second outlet opening is in fluid communication with a second base of a second well of the port at a second depth from the proximal surface different from the first depth;
   connecting the dual lumen catheter to the first and second outlet openings;
   providing a first fluid to the first well; and
   providing a second fluid to the second well.

2. The method according to claim 1, wherein fluid is provided to the first well by piercing a septum covering the first well with a needle.

3. The method according to claim 1, wherein the first and second wells and the first and second inlet openings are separated so that the first and second fluids remain separated until after they have left the port.

4. The method according to claim 3, wherein the port is implanted subcutaneously with a proximal surface thereof facing outward, each of the first and second wells including an opening formed in the proximal surface.

5. The method according to claim 4, wherein the first and second outlet openings are positioned relative to one another so that, when the port is implanted, the first outlet opening is closer to an outer surface of the skin than the second outlet opening.

6. The method according to claim 5, wherein the first and second outlet openings are coupled to the first and second wells by first and second channels, respectively and wherein, when the port is implanted, the first channel is closer to the outer surface of the skin than the second channel.

7. The method according to claim 4, wherein the first and second outlet openings are positioned relative to one another so that, when the port is implanted, the first and second openings are substantially equidistant from an outer surface of the skin.

8. The method according to claim 7, wherein the first and second outlet openings are coupled to the first and second wells by first and second channels, respectively and wherein, when the port is implanted, the first and second channels are substantially equidistant from the outer surface of the skin and wherein the first channel extends around a perimeter of the second well.

* * * * *